(12) United States Patent
Blake, III

(10) Patent No.: US 11,532,078 B2
(45) Date of Patent: *Dec. 20, 2022

(54) SYSTEMS AND METHODS FOR IDENTIFYING OPTIMIZED ABLATION TARGETS FOR TREATING AND PREVENTING ARRHYTHMIAS SUSTAINED BY REENTRANT CIRCUIT

(71) Applicant: CARDIOSOLV ABLATION TECHNOLOGIES, INC., Boston, MA (US)

(72) Inventor: Robert Clayton Blake, III, Mountain House, CA (US)

(73) Assignee: CardioSolv Ablation Technologies, Inc., Boston, MA (US)

( * ) Notice: Subject to any disclaimer, the term of this patent is extended or adjusted under 35 U.S.C. 154(b) by 108 days.

This patent is subject to a terminal disclaimer.

(21) Appl. No.: 16/872,426

(22) Filed: May 12, 2020

(65) Prior Publication Data

US 2020/0273170 A1  Aug. 27, 2020

Related U.S. Application Data

(63) Continuation of application No. 16/548,880, filed on Aug. 23, 2019, now Pat. No. 10,679,348, which is a
(Continued)

(51) Int. Cl.
*G06T 7/00* (2017.01)
*A61B 5/319* (2021.01)
(Continued)

(52) U.S. Cl.
CPC ............ *G06T 7/0012* (2013.01); *A61B 5/319* (2021.01); *G06T 7/11* (2017.01); *G06T 7/13* (2017.01);
(Continued)

(58) Field of Classification Search
CPC . G06T 7/0012; G06T 7/11; G06T 7/13; G06T 2207/10088; G06T 2207/30048;
(Continued)

(56) References Cited

U.S. PATENT DOCUMENTS 10,402,966 B2 * 9/2019 Blake, III .................. G06T 7/13
10,679,348 B2 * 6/2020 Blake, III ............. G06T 7/0012
(Continued)

OTHER PUBLICATIONS

Musha et al. "Dynamic Simulation of Electrical Phenomena in the Human Heart." Images of the Twenty-First Century, Proceedings of the Annual International Engineering in Medicine and Biology Society, Nov. 9, 1989, 2 pages (Year: 1989).*

(Continued)

*Primary Examiner* — Jon Chang
(74) *Attorney, Agent, or Firm* — Finnegan, Henderson, Farabow, Garrett & Dunner LLP

(57) ABSTRACT

Methods and systems for identifying optimized ablation targets for treating and preventing arrhythmias sustained by reentrant circuits are described. The methods comprise receiving at least one mesh generated from one or more images of a patient's heart, receiving activation data generated from one or more simulations of electrical-signal propagation over the at least one mesh, generating at least one flow graph based on the activation data and the at least one mesh, and applying a max-flow min-cut algorithm to the at least one flow graph to determine at least one of a number, one or more dimensions, and one or more locations of one or more ablation targets. Non-transitory computer-readable media storing a set of instructions for treating and preventing arrhythmias sustained by reentrant circuits are also described.

19 Claims, 10 Drawing Sheets

Related U.S. Application Data continuation of application No. 15/368,588, filed on Dec. 3, 2016, now Pat. No. 10,402,966.

(60) Provisional application No. 62/262,874, filed on Dec. 3, 2015.

(51) Int. Cl.
| | | |
|---|---|---|
| *G06T 7/11* | (2017.01) | |
| *G06T 7/13* | (2017.01) | |
| *A61B 5/055* | (2006.01) | |
| *A61B 18/00* | (2006.01) | |
| *A61B 5/349* | (2021.01) | |
| *A61B 5/363* | (2021.01) | |

(52) U.S. Cl.
CPC .............. *A61B 5/055* (2013.01); *A61B 5/349* (2021.01); *A61B 5/363* (2021.01); *A61B 18/00* (2013.01); *A61B 2576/023* (2013.01); *G06T 2207/10088* (2013.01); *G06T 2207/30048* (2013.01)

(58) Field of Classification Search
CPC ......... A61B 5/319; A61B 5/055; A61B 5/349; A61B 5/363; A61B 18/00; A61B 2576/023; G16H 30/40
See application file for complete search history.

(56) References Cited

U.S. PATENT DOCUMENTS

2017/0109496 A1* 4/2017 Hisada ................. G16H 50/50
2018/0103865 A1    4/2018 Trayanova

OTHER PUBLICATIONS

Barta et al. "3D Simulation of the Electrical Activity Patterns in the Ischemic Heart." Proceedings, Computers in Cardiology, Sep. 19, 1989 (Year: 1989).*

Zhao et al. "Image-Based Model of Atrial Anatomy and Electrical Activation: A Computational Platform for Investigating Atrial Arrhythmia." IEEE Transactions on Medical Imaging, vol. 32, No. 1, Jan. 2013, pp. 18-27 (Year: 2013).*

Tobon et al. "Vulnerability for Reentry in a Three Dimensional Model of Human Atria: A Simulation Study." Annual International Conference of the IEEE Engineering in Medicine and Biology, Aug. 31, 2010, pp. 224-227 (Year: 2010).*

Uzkent et al. "3-D MRI Cardiac Segmentation Using graph Cuts." IEEE Western New York Image and Signal Processing Workshop, Nov. 7, 2014, pp. 47-51 (Year: 2014).*

Boykov et al. "An Experimental Comparison of Min-Cut/Max-Flow Algorithms for Energy Minimization in Vision." IEEE Transactions on Pattern Analysis and machine Intelligence, vol. 26, No. 9, Sep. 2004, pp. 1124-1137 (Year: 2004).*

* cited by examiner

SYSTEMS AND METHODS FOR IDENTIFYING OPTIMIZED ABLATION TARGETS FOR TREATING AND PREVENTING ARRHYTHMIAS SUSTAINED BY REENTRANT CIRCUIT

PRIORITY CLAIM

This application is a continuation of U.S. patent application Ser. No. 16/548,880, filed Aug. 23, 2019, which is a continuation of U.S. patent application Ser. No. 15/368,588, filed on Dec. 3, 2016 (issued on Sep. 3, 2019 as U.S. Pat. No. 10,402,966), which claims priority from U.S. Provisional Patent Application No. 62/262,874 filed on Dec. 3, 2015, which is hereby incorporated by reference in its entirety in the present application.

TECHNICAL FIELD

The present disclosure relates generally to systems and methods for identifying optimized ablation targets for treating and preventing arrhythmias sustained by reentrant circuits.

BACKGROUND

Catheter ablation is a therapy for various cardiac arrhythmias. Cardiac arrhythmia is a condition in which an organism's heart beats too quickly, too slowly, or in an irregular (e.g., non-periodic) manner. A more precise name for the condition in which the heart beats too quickly is "tachycardia." A diagnosis of tachycardia may be given for a heartrate above a certain value (e.g., 100 beats per minute, or bpm, in adults). Tachycardia that originates in the ventricular region of the heart may be referred to as "ventricular tachycardia," or "VT."

One variety of VT is named "reentrant VT." Reentrant VT is characterized by improper electrical-signal propagation through the heart-muscle cells, or "cardiomyocytes." This may occur when cardiomyocytes are stressed or irritated by, for example, ischemia (i.e., an inadequate blood supply caused by, for example, a myocardial infarction), tissue necrosis, drug reactions, or electrolyte imbalances. Such irritation may alter conduction patterns in the heart and/or the conduction speed and refractory period of the affected cardiomyocytes, resulting in improper electrical-signal propagation. The improper pathways the electrical signal takes are "reentrant pathways" or "reentrant circuits." Reentrant pathways may be created also when a scar develops on the heart tissue, such as following a myocardial infarction. Reentrant pathways are closed pathways (e.g., a loop or circuit).

When the electrical signal takes a reentrant pathway, the ventricles may contract and cause a heartbeat at an improper time and rate. A second propagation of an electrical signal over heart tissue following a recent first propagation does not, however, necessarily trigger an extra heartbeat; no contraction of the ventricles is triggered if an electrical signal propagates during a refractory period of the cardiomyocytes. A scar on the heart tissue, however, may create a large obstacle for the electrical signal to propagate around. If the path around the scar is long enough, the electrical signal may take longer to travel around the scar than the refractory period of the cardiomyocytes. This may result in the cardiomyocytes around the scar being constantly activated by the electrical signal travelling on a reentrant pathway around the scar, thus resulting in an arrhythmia. A scar on the heart tissue may also itself conduct electrical signals through microchannels therein, potentially forming reentrant pathways.

Catheter ablation is the process of using a catheter to, among other things, burn or freeze cardiomyocytes that form a reentrant pathway, creating scar tissue that will not conduct or causing a scar to conduct much less than before ablation. Severing the reentrant pathway may prevent the electrical signal from propagating down the reentrant pathway and triggering a heartbeat at an improper time and rate.

Determining the location or locations for ablation on the heart tissue presents various difficulties. In making this determination, one may seek to minimize the amount of heart tissue burned or frozen when attempting to treat the tachycardia. Each lesion intentionally created by burning or freezing involves a risk of collateral injury to the heart, such as, for example, one or more steam pops, perforations, and tamponades. Instead or in addition, one may seek to minimize the number of ablations in order to limit the duration of the ablation procedure. Longer ablation procedures are associated with increased risk of chamber perforation, thromboemboli, bleeding, and radiation overexposure.

Because reentrant pathways are three-dimensional (3D) and may assume complicated shapes, determining the location or locations of ablation such that their number and size is minimized presents difficulties. One method is to insert a catheter into the heart and record the voltage at the catheter's tip at each position in space to build a static surface representation of the heart and the voltages thereon. The resulting images can be difficult to understand because the electrical signal changes constantly on the heart's surface and such changes may not be captured by the static surface representation. Additionally, there is no consensus in the medical community on the proper method for picking ablation locations based on the static surface representations. This method and other methods requiring catheter-based mapping are very time-consuming and error-prone because the catheter must be placed on or near every relevant spot on the heart. In addition, these methods do not ignore pathways that are not reentrant (e.g., dead-end pathways). Another method for determining the location or locations of ablations comprises stimulating cardiac tissue with a catheter tip and recording an electrocardiograph (ECG). The recorded ECG may be compared to a second ECG that captures the arrhythmic activity to attempt determining whether the catheter tip was on a reentrant pathway. Even if this comparison reveals a reentrant pathway, it does not indicate where to ablate.

Other methods using software-run 3D simulations are being explored to determine ablation targets. Using software-run 3D simulations may overcome many of the deficiencies of the foregoing methods. Software-run 3D simulations may overcome many of the deficiencies because they enable processing of large amounts of information in short periods of time without manual human intervention, leading to fewer missed spots and errors in data collection inherent in the previously discussed methods. Using simulations, unlike other methods, may not require catheter mapping or heart stimulation. Currently, however, when presented with simulation data describing the electrical-signal propagation on and through heart tissue over time in a 3D simulation, clinicians may have trouble picking ablation locations such that the number and size of ablations is minimized. To pick an ablation location, electrical-signal levels may need to be repeatedly observed in the simulation at many or all locations in the ventricle simulation at many or all points in time for which data is available. Picking an ablation location with this process is further complicated by the fact that the electrical signal may propagate not only along the inner and outer surface of the tissue but also within or through the tissue. Picking an ablation location by observing the simulation may also be difficult because the simulation shows electrical-signal propagation along pathways that eventually get blocked by, for example, a scar or cardiomyocytes in their refractory period. Such blocked propagations may obscure actual reentrant pathways the clinicians seek to find in the simulation. FIG. 1A and FIG. 1B are illustrations of exemplary 3D simulation views of electrical-signal propagation on and through a heart 100a and 100b, respectively. A clinician may attempt to observe views 100a and 100b to determine optimal ablation locations. Catheter-ablation locations (i.e., ablation targets) are optimal if they are at locations requiring the fewest and smallest ablations to treat and prevent future arrhythmia. Views 100a and 100b show electrical-signal propagations that may eventually get blocked by, for example, scar tissue, and therefore highlight pathways that are not reentrant pathways. Additionally, a clinician may need to observe cross sections of views 100a and 100b to study the electrical signal propagation through the heart tissue's interior. Because of the quantity of information presented in views 100a and 100b, isolating the reentrant pathways and finding the optimal ablation locations may be very time-consuming or impossible.

The requisite observations in a software-based simulation may be very time-consuming and, if many locations are not observed at many points of time, may lead to over-selection of locations for ablation than necessary to treat the VT, or selection of locations that do not help treat the VT. Even if a clinician observes the electrical-signal propagation at all locations at all points of time, he or she may need to consider this enormous amount of information simultaneously to determine the proper locations to ablate and the proper ablation size. Success in this process requires much training, intuition, and expertise on the part of the clinician. This decreases the number of clinicians available to perform the analysis and increases procedure costs. Even with requisite training and expertise, clinicians may make errors when picking ablation locations based on observations of a simulation. The use of software-based simulations may have the benefit of providing clinicians with more data and data that is more accurate, but it may overwhelm and obscure the information the clinician is looking for.

The disclosed systems and methods are directed to overcoming one or more of the problems set forth above and/or other problems or shortcomings in the prior art.

SUMMARY

The present disclosure is directed to systems and methods for identifying optimized ablation targets for treating and preventing arrhythmias sustained by reentrant circuits.

Consistent with at least one disclosed embodiment, a method is disclosed for identifying optimized ablation targets for treating and preventing arrhythmias sustained by reentrant circuits. The method may include receiving at least one mesh generated from one or more images of a patient's heart. The method may also include receiving activation data generated from one or more simulations of electrical-signal propagation over the at least one mesh. The method may further include generating at least one flow graph based on the activation data and the at least one mesh. The method may also include applying a max-flow min-cut algorithm to the at least one flow graph to determine at least one of a number, one or more dimensions, and one or more locations of one or more ablation targets.

In certain embodiments, the at least one mesh may comprise one or more elements. In exemplary embodiments, the activation data may comprise one or more activation times associated with one or more parts of the elements. In an embodiment, the at least one flow graph may comprise one or more nodes associated with the one or more elements.

Identifying optimized ablation targets may also include designating one or more nodes as source nodes and designating one or more nodes as sink nodes. In certain embodiments, the at least one flow graph may comprise one or more edges connecting two or more nodes associated with one or more elements. In an exemplary embodiment, the one or more edges ma connect two or more nodes associated with two or more elements that are joined.

Identifying optimized ablation targets may also include calculating one or more capacity associated with the one or more edges. Identifying optimized ablation targets may also include calculating one or more capacity associated with the one or more edges; creating a combination of nodes; and designating the combination of nodes as a source, wherein the combination is created such that the combination comprises the smallest number of nodes and the sum of the one or more capacities associated with the one or more edges emanating from the nodes in the combination is above a threshold.

Identifying optimized ablation targets may also include calculating one or more capacity associated with the one or more edges; creating a combination of nodes; and designating the combination of nodes as a sink, wherein the combination is created such that the combination comprises the smallest number of nodes and the sum of the one or more capacities associated with the one or more edges terminating into the nodes in the combination is above a threshold.

Identifying optimized ablation targets may also include calculating one or more capacity associated with the one or more edges; creating a combination of nodes; and designating the combination of nodes as a source, wherein the combination is created such that the combination comprises the smallest number of nodes and edges emanating from nodes in the combination have non-zero residual capacities.

Identifying optimized ablation targets may also include calculating one or more capacity associated with the one or more edges; creating a combination of nodes; and designating the combination of nodes as a sink, wherein the combination is created such that the combination comprises the smallest number of nodes and edges terminating into nodes in the combination have non-zero residual capacities.

Identifying optimized ablation targets may also include determining one or more directions for the one or more edges. Identifying optimized ablation targets may also include determining one or more residual capacities for one or more edges. Identifying optimized ablation targets may also include eliminating one or more edges that do not form part of a path from a source node to a sink node. Identifying optimized ablation targets may also include displaying the at least one of a number, one or more dimensions, and one or more locations of one or more ablation targets.

Identifying optimized ablation targets may also include creating at least two flow-graph segments out of at least one flow-graph by removing an edge from the flow graph, adding a source to one of at least two flow-graph segments, and adding a sink to one of at least two flow-graph segments. In certain embodiments, one or more nodes may be associated with elements that were activated within one or more time windows. In an exemplary embodiment, the one or more nodes may be associated with elements that were activated at one or more times.

Identification of optimized ablation targets may also include determining whether a reentrant pathway is present. In certain embodiments, the one or more capacities may be based on one or more measures of intersection of the two or more elements that are joined.

In another aspect, the present disclosure is directed to a system for identifying optimized ablation targets for treating and preventing arrhythmias sustained by reentrant circuits. The system may include a memory device and a central processing unit (CPU). The CPU may programmed with instructions to receive at least one mesh generated from one or more images of a patient's heart. The CPU may also be programmed with instructions to receive activation data generated from one or more simulations of electrical-signal propagation over the at least one mesh and generate at least one flow graph based on the activation data and the at least one mesh. The CPU may also be programmed with instructions to apply a max-flow min-cut algorithm to the at least one flow graph to determine at least one of a number, one or more dimensions, and one or more locations of one or more ablation targets.

In another aspect, the present disclosure may be directed to non-transitory computer-readable medium storing a set of instructions that are executable by one or more processors to cause the one or more processors to perform a method for identifying optimized ablation targets for treating and preventing arrhythmias sustained by reentrant circuits. The method may include receiving at least one mesh generated from one or more images of a patient's heart. The method may further include receiving activation data generated from one or more simulations of electrical-signal propagation over the at least one mesh. The method may also include generating at least one flow graph based on the activation data and the at least one mesh. The method may further include applying a max-flow min-cut algorithm to the at least one flow graph to determine at least one of a number, one or more dimensions, and one or more locations of one or more ablation targets.

Other embodiments of this disclosure are disclosed in the accompanying drawings, descriptions, and claims. Thus, this summary is exemplary only, and is not to be considered restrictive.

BRIEF DESCRIPTION OF THE DRAWINGS

The accompanying drawings, which are incorporated in and constitute a part of this specification, illustrate the disclosed embodiments and, together with the description, serve to explain the principles of the various aspects of the disclosed embodiments. In the drawings.

It is to be understood that both the foregoing general descriptions and the following detailed descriptions are exemplary and explanatory only and are not restrictive of the claims.

DESCRIPTION OF EXEMPLARY EMBODIMENTS

Reference will now be made to certain embodiments consistent with the present disclosure, examples of which are illustrated in the accompanying drawings. Wherever possible, the same reference numbers will be used throughout the drawings to refer to same or like parts.

The present disclosure describes systems and methods for identifying optimized ablation targets for treating and preventing arrhythmias sustained by reentrant circuits. Such systems and methods may generate a flow graph based on simulation data run over a polyhedral mesh in 3D space, which may be a volumetric mesh, of a patient's heart. The mesh may comprise polyhedrons of any variety, including, but not limited to, tetrahedrons and/or hexahedrons. In certain embodiments, the mesh may be a polygon mesh or a mesh of another variety. A max-flow min-cut algorithm (MFMC algorithm), or any variation thereof, may be run over the flow graph to determine the minimum number and minimum size of ablations necessary to terminate electrical-signal propagation over reentrant pathways. Such systems and methods may be used before and/or during ablation treatment to identify one or more ablation targets. The methods may be performed once before or during treatment or may be performed multiple times before and/or throughout a treatment procedure.

Figure 1B:
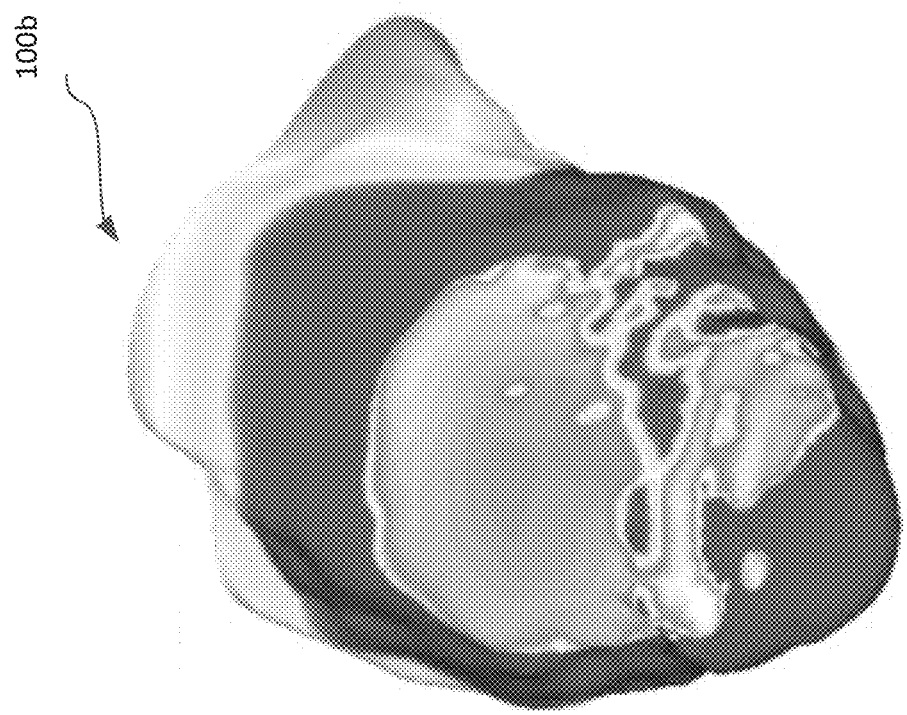
FIG. 1B: Illustrates an exemplary 3D simulation view of electrical-signal propagation on and through a heart.
Figure 1A:
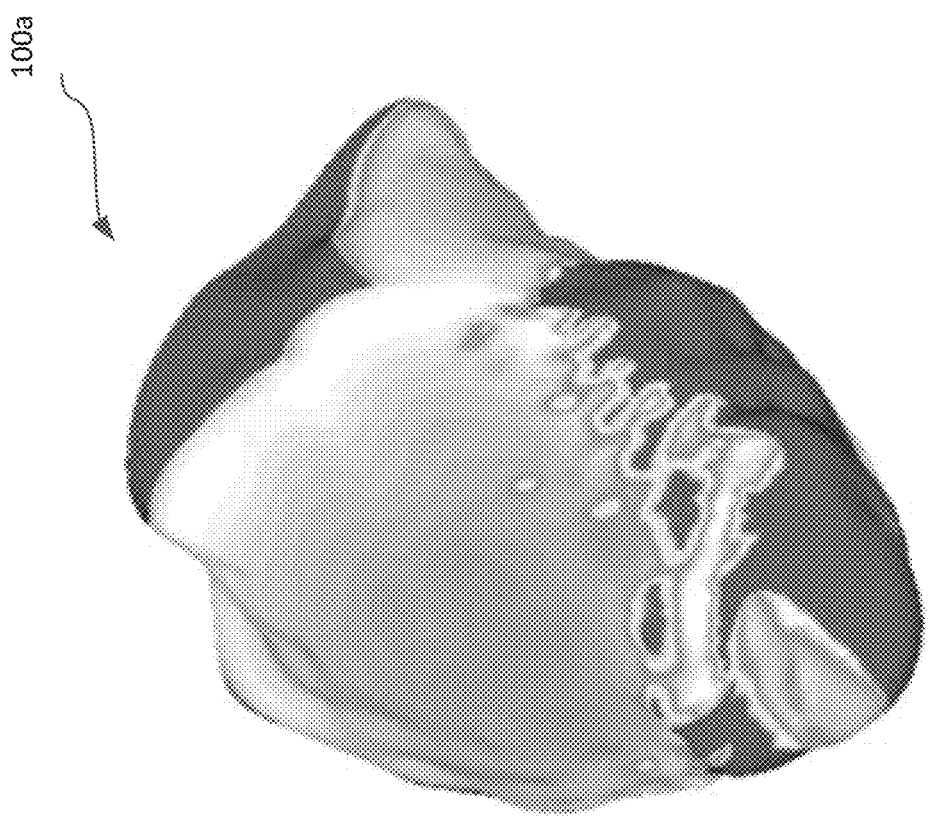
FIG. 1A: Illustrates an exemplary 3D simulation view of electrical-signal propagation on and through a heart.
Figure 2:
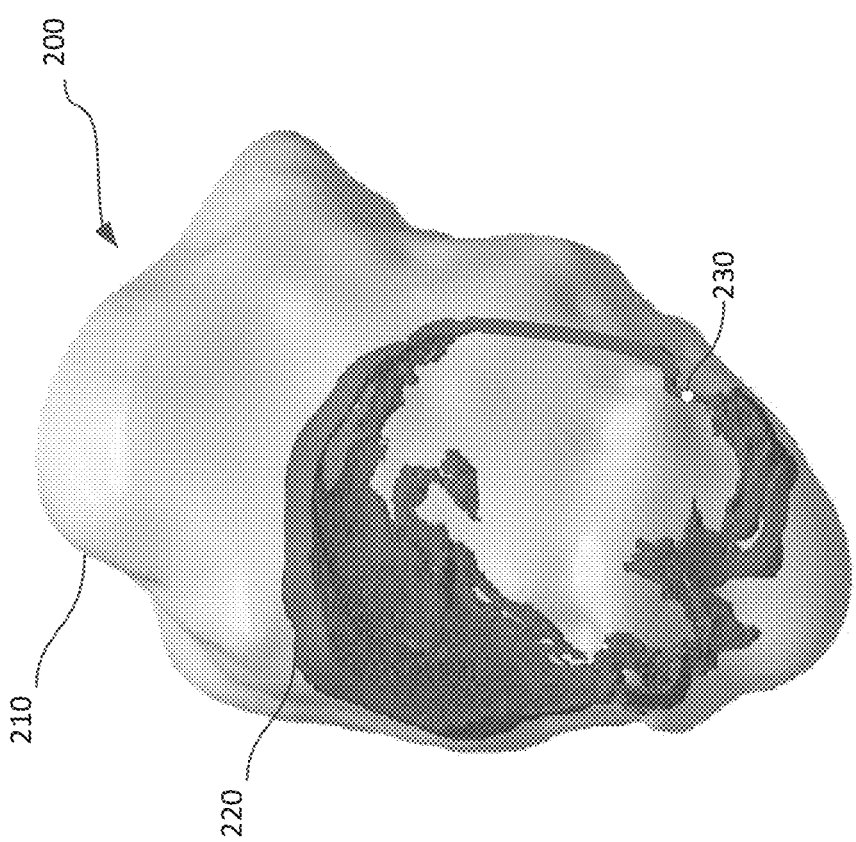
FIG. 2: Illustrates an exemplary reentrant circuit and optimized ablation target display.

Software-run 3D simulations of electrical-signal propagation across heart tissue may be useful in identifying, treating, and preventing arrhythmias sustained by reentrant circuits if the simulations minimize non-pertinent data and calculate optimized catheter-ablation targets. FIG. 2 is an illustration of an exemplary reentrant circuit and optimized ablation target display 200. Display 200 may comprise one or more 3D models of a heart or heart tissue 210, one or more reentrant pathway 220, and one or more optimal catheter-ablation target 230. Catheter-ablation targets (i.e., ablation targets) are optimal if they are at locations requiring the fewest and smallest ablations to treat and prevent future arrhythmia.

Figure 3:
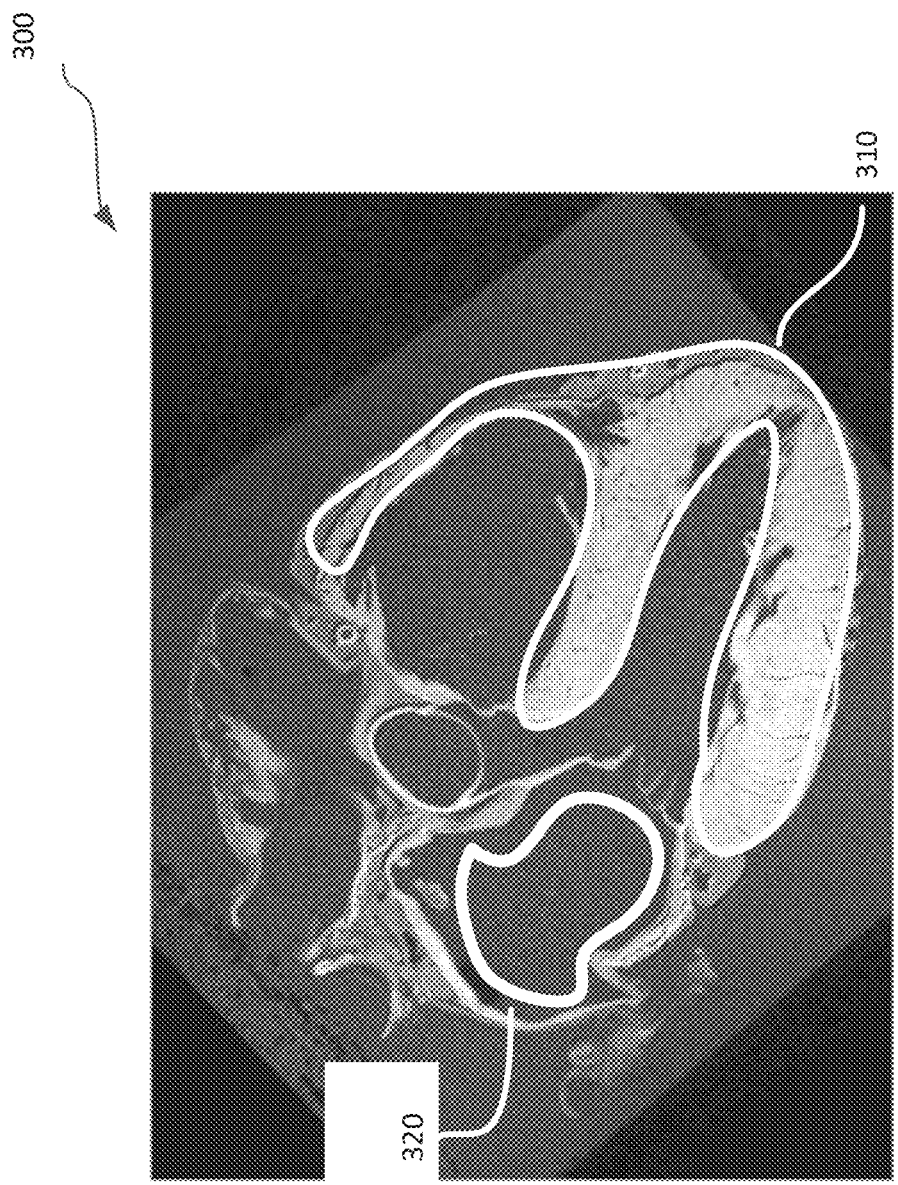
FIG. 3: Illustrates an exemplary MRI.

The identification of an optimal ablation target or targets may, in illustrative embodiments, be performed by a system capable of generating a flow graph from a simulation of electrical-signal propagation over a patient's heart tissue. The simulation may be run over a polyhedral mesh constructed from one or more cardiac imaging modalities—such as, for example, Magnetic Resonance Images (MRIs), echocardiographic images, and/or computerized tomography scans—of the patient's heart. FIG. 3 is an illustration of an exemplary MRI 300. The one or more MRIs 300 may be input into processing software. This inputting may be performed by an image-scanning device, by sending MRIs 300 over a network to a connected computer running the processing software, or other conventional image-inputting means. Once input into the processing software, MRIs 300 may be segmented into various components by identifying exemplary sections 310 and 320 of the MRI to the processing software. Exemplary section 310 may indicate ventricular tissue and exemplary section 320 may indicate blood in an atrial cavity. Sections of the MRIs may be identified as, for example, one or more of the following: healthy tissue, a scar, a border zone between different parts of the heart, and blood in cavities. The segmentation may be performed by software configured to identify sections of the MRIs, by a user, or a combination of both.

Figure 4:
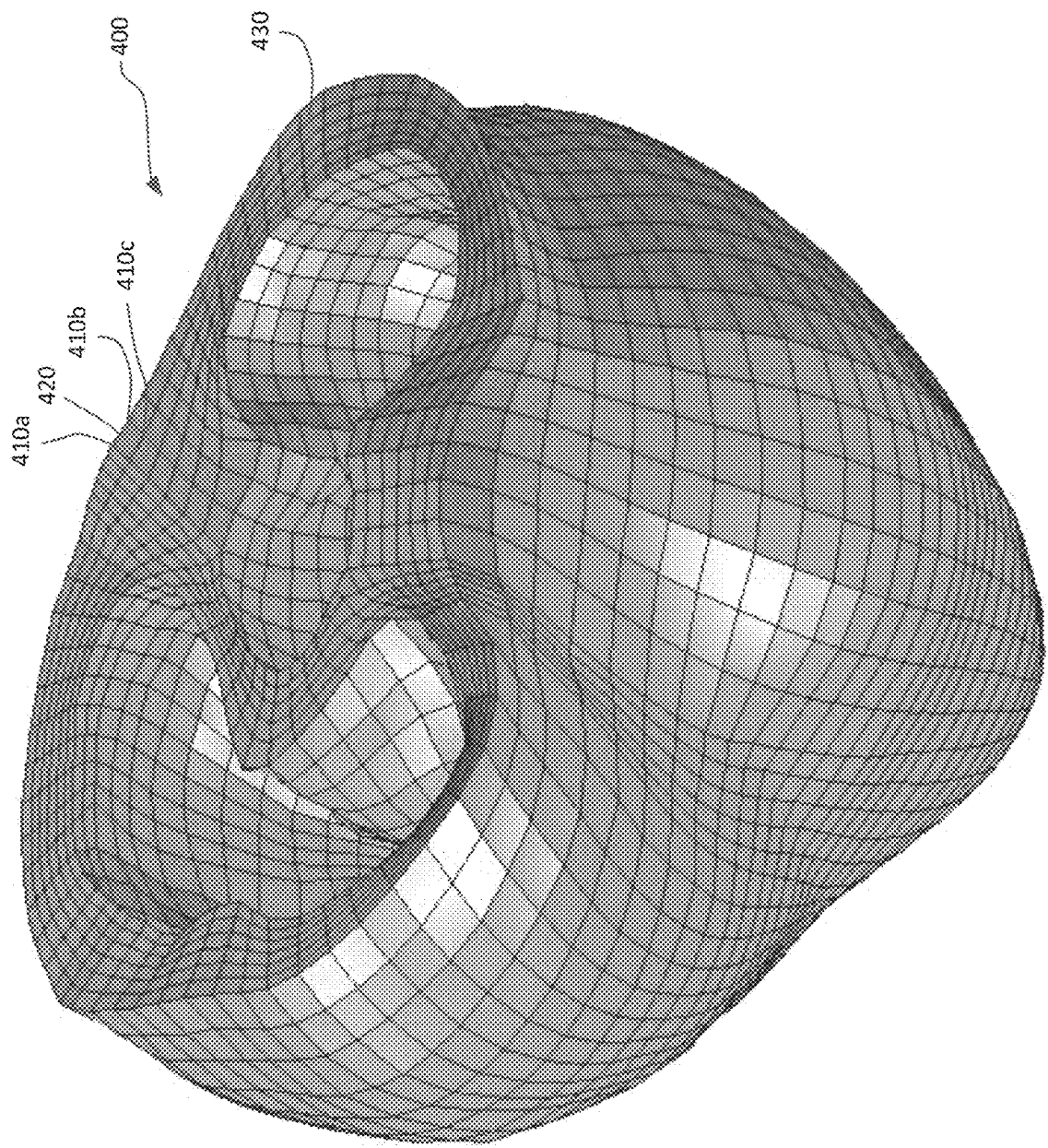
FIG. 4: Illustrates an exemplary polyhedral mesh.

The one or more segmented MRIs may be used to generate a polyhedral mesh of the patient's heart. FIG. 4 is an illustration of an exemplary polyhedral mesh 400 of a section of a patient's heart. In certain embodiments, the mesh may be a digitally generated mesh. The polyhedral mesh may be a collection of vertices (such as exemplary vertices 410a, 410b, and 410c) and edges (such as exemplary edge 420), and may be a structured, an unstructured, or both a structured and an unstructured grid. Vertices 410a, 410b, and 410c may be points in 3D space. Edge 420 may be a connection between two vertices such as vertices 410a and 410b. The set of closed edges may define polyhedrons, such as exemplary polyhedron 430. Polyhedron 430 may be the building block, or "element," of polyhedral mesh (i.e., mesh) 400. In certain embodiments, if the mesh were a polygon mesh, a polygon would be the building block. In the case of a polyhedron mesh, the polyhedrons may be, but are not limited to, for example, tetrahedrons, hexahedrons, or a mixture of different types of polyhedrons. Polyhedral mesh 400 may be a conformal mesh. In certain embodiments, polyhedral mesh 400 may be a non-conformal mesh. Because adjacent polyhedral elements may be joined by a planar face with an appropriate number of sides in structured and unstructured meshes, various methods for calculating the area of a two-dimensional polygon may be used to calculate the cross-sectional area of the interface between two three-dimensional polyhedral elements. For examples, for a triangle, this could be one-half multiplied by the length of the base multiplied by the height. Alternatively, the area of a triangle may be computed as one-half the magnitude of the cross-product of two intersecting sides of the triangle. Similarly, the area of a rectangular interface between two elements may be computed as the magnitude of the cross-product of two intersecting edges of the rectangle. In the case of a polygon mesh, adjacent polygons may be joined by an edge, the length of which may be calculated.

In the illustrative simulation software, one or more virtual electrodes may be placed on the mesh. A user may specify in the software the virtual electrical stimulation to the heart mesh model when the simulation is run. The stimulation may be specified for the one or more electrodes. The stimulation may be specified in such a manner that electrical-signal propagation occurs in the simulation consistent with arrhythmia. As the region of interest may be around a scar and/or a border zone tissue, stimulations may be located near the periphery of the scar, such as at several locations evenly spaced around the boundary of the scar. Other typical locations for stimulation may be the right-ventricular outflow tract and right-ventricular apex, as these may be convenient locations for catheter-based stimulation of the heart in a clinical environment. Stimulation strength may be a multiple of the minimum current required to activate simulated tissue at rest, modeled by direct current injection to the cellular ionic models used in the mesh (e.g., two or three times the minimum current). For example, the electrodes may stimulate the heart mesh model in the simulation so electrical-signal propagation consistent with ventricular tachycardia, or other relevant arrhythmia, is present in the simulation. Simulations that continue to exhibit activity (e.g., electrical-signal propagation) after termination of externally-applied pacing may be considered successful initiations of reentrant arrhythmia without further observation of the simulation data. In certain embodiments, full simulation data may be visualized and analyzed in detail to verify initiation of reentrant arrhythmia.

Running the illustrative simulation may generate activation data. This data may comprise a list of times the simulation detected a voltage above a certain threshold at one or more vertices in the mesh (i.e., activation times). This threshold may be ionic-model dependent and may indicate an "activation" spike above the transmembrane voltage observed in a cardiac cell at rest (e.g., greater than −10 mV). In some embodiments, some function of the voltage threshold and a rate of change of the transmembrane voltage (e.g., dV/dt) may be employed to eliminate false detections of activations that may stem from high current driven into a refractory cell. The activation data may comprise the list of vertices associated with the times the voltage was detected to be above the threshold at the respective vertices. The vertices and/or their activation times may be sorted from the earliest activated to the latest activated.

Figure 5:
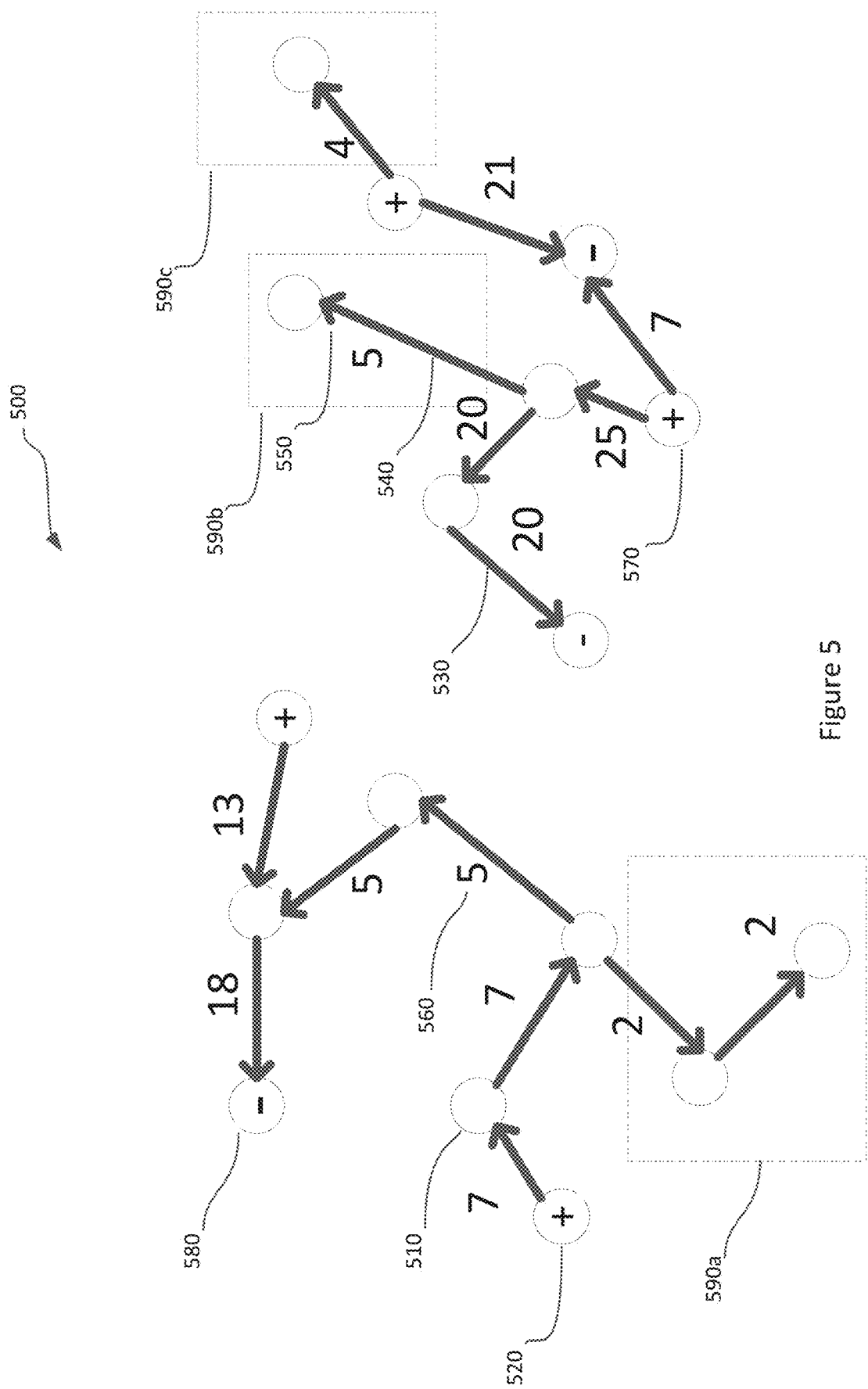
FIG. 5: Illustrates an exemplary flow graph.

Using the activation data and mesh, the system, according to an exemplary embodiment, may generate a flow graph for identifying ablation targets, such as exemplary flow graph 500 illustrated in FIG. 5. This may be accomplished using, for example, exemplary process 600 illustrated in FIG. 6. In certain embodiments the activation data may be provided directly by the patient or other source independent of a simulation. The flow graph 500 (also referred to as a flow network) may be a directed graph, made up of nodes (e.g., points), such as exemplary nodes 510 and 520, and edges, such as exemplary edges 530 and 540, connecting two or more nodes. In certain embodiments, flow graph 500 may be an undirected graph. Nodes may represent structures, such as polyhedron 430 of polyhedral mesh 400 in FIG. 4. A pair of nodes may be connected by an edge if there is capacity for movement of something between the structures represented by the pair of nodes. The capacity for movement, as referenced herein, may, in some embodiments, refer to a capability of electrical-signal to propagate. The edges may have one or more directions associated with them, indicating one or more directions of the capacity for movement or the net capacity for movement between the structures associated with the nodes connected by the edges. Such one or more directions may be visualized as one or more arrowheads, such as exemplary arrowhead 550, pointing toward the one or more directions of the capacity for movement. One or more edges may have one or more capacities associated with them, such as exemplary flow capacity 560, indicating the largest possible flow between the structures associated with the nodes connected by the edges as determined by, for example, the cross-sectional area of the common face between the structures. In the case of a polygon mesh or a mesh comprising elements of other varieties, the length of the common edge between the polygons or other common structure may determine the capacity in the corresponding flow-graph edge. One or more edges may have a maximum flow amount (i.e., maximum flow) associated with them, describing how much net movement would occur between structures associated with the nodes connected by the edges if there was a maximum net movement between the source and the sink. The flow graph may contain a source, such as exemplary source 570, and/or a sink, such as exemplary sink 580, representing nodes that only have movement coming out of them or only have movement coming into them, respectively, and their associated structures.

Figure 6:
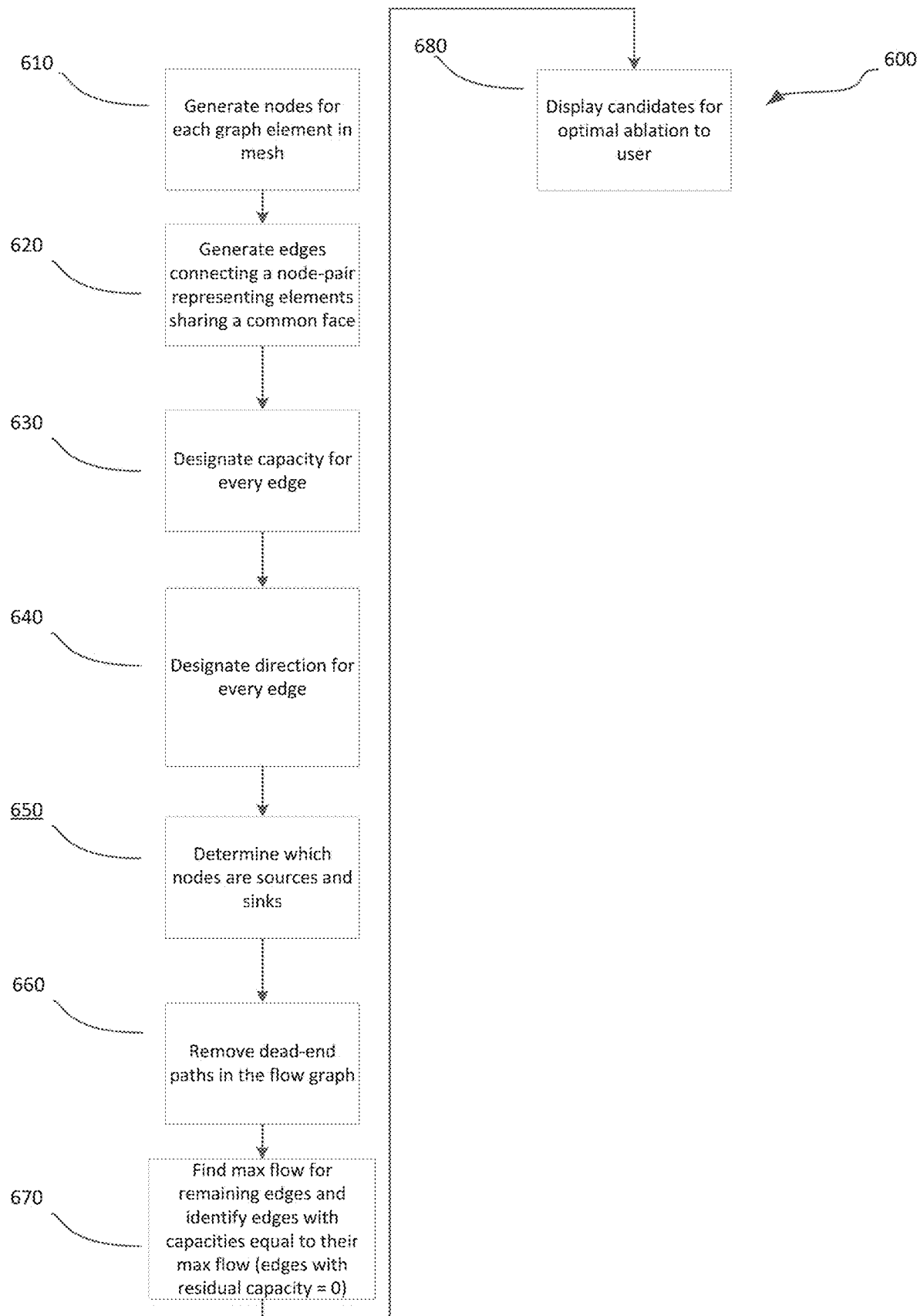
FIG. 6: Illustrates an exemplary process for identifying optimized ablation targets for treating and preventing arrhythmias sustained by reentrant circuits.

The exemplary system may generate flow-graph nodes for each element in the mesh (e.g., for each tetrahedron) at step 610 of exemplary process 600, illustrated in FIG. 6. In some embodiments, the system may generate a node only for the elements that were activated. An element may be considered activated if, for example, one or more vertices comprising the element were activated. Other methods of determining whether an element was activated may be used. In some embodiments, the system may generate nodes only for elements that were activated at a time that is a multiple of a fixed period (e.g., elements that were activated every 30 milliseconds from the start of the simulation, such as at 30 milliseconds, 60 milliseconds, 90 milliseconds, etc.). An element may be determined to be activated at a particular time using a function of the times at which one or more vertices in the element were activated, such as the average time the element's vertices were activated. The fixed period may be set higher for lower resolution (i.e., fewer nodes) and faster processing or set lower for higher resolution (i.e., more nodes) but slower processing. In some embodiments, the system may generate one or more nodes for one or more elements that were activated within a window of time. In some embodiments, a single node may be generated for multiple elements. In such case, the elements associated with the node may be those that were activated at a certain time or within one or more windows of time. This may be referred to as "binning." For example, a node may be generated for all elements activated within every 10 millisecond window from the beginning to the end of the simulation. Such method may allow for output ablation targets to be of sufficient size and proximity to one another to prevent arrhythmia. The size of the window may be fixed or varied. In some embodiments, a node may be generated for all elements activated within one or more windows of time and that are within a fixed or variable distance from one another.

The system, according to an illustrative embodiment, may generate edges connecting node-pairs at step 620. The edges may be generated if the elements represented by the node-pairs share a common face (e.g., two tetrahedrons having one side in common) and if the difference in activation time of the two elements was below a threshold time (e.g., 30 milliseconds). In certain embodiments, the difference in activation time may itself determine that two nodes are connected. In certain embodiments, the sharing of a common face by elements represented by the node-pairs is sufficient to connect the two nodes. Whether two elements have a common face may be determined by examining the mesh. This examination may comprise determining whether two elements share a number of vertices equal to the number of sides the elements' faces have. The activation time for a single element may be determined as a function of the activation times of the vertices the element consists of (e.g., the average of the activation times at the vertices of a tetrahedron). The activation times for individual vertices may be looked up in the activation data. The difference in activation time between two elements may be determined by subtracting the activation time of one element from the activation time of the other. Other methods of determining whether an element was activated and the time it was activated may be used. In an exemplary embodiment, an edge may be associated with a plurality of common faces. This may occur if, for example, these common faces are parts of a plurality of elements that are associated with a single node. In certain embodiments, this may occur when binning is performed. In certain embodiments, other methods for connecting node-pairs representing adjacent elements may be used.

The exemplary system may determine capacities for edges connecting two nodes at step 630. The edge capacities may be determined using, for example, a function of the cross-sectional area of the common face between the two elements represented by the two nodes (e.g., rounding the cross-sectional area to the nearest integer). In certain embodiments, the capacity for an edge connecting two nodes may be determined by dividing the area of the common face associated with the edge by a number (e.g., a small number) to produce an unsigned integer. Doing so may facilitate computing the maximum flow, as discussed below, by making the problem of calculating the maximum flow tractable. The method for calculating the edge capacity and the units used to represent edge capacity may be irrelevant as long as they are applied consistently for all edges. In certain embodiments, an edge that is associated with a plurality of common faces may have an edge capacity that is a function of the cross-sectional areas of the common faces it is associated with, such as the sum of the cross-sectional areas of the common faces. The may occur when, for example, binning is performed.

In certain embodiments, the system may determine one or more directions of the edges at step 640. A direction for a given edge may indicate, for example, which of the two elements represented by the connected nodes had an activation after the other (this may be visualized as, for example, an arrow from the first-activated node to the second-activated node).

The illustrative system may determine which nodes are sources and which nodes are sinks at step 650. The nodes identified as sources may be those representing elements comprising one or more activated vertices at the time the simulation began, or nodes that were generated after an edge was removed and designated as sources, as discussed in a forthcoming section. The nodes identified as sinks may be those representing elements comprising one or more activated vertices at the time the simulation ended, or nodes that were generated after an edge was removed and designated as sinks, as discussed in a forthcoming section. In some embodiments, a combination of nodes may be combined to form a single source or sink. For example, if running a max-flow min-cut algorithm over the flow graph, as discussed below, indicates that edges emanating from the source should be removed, one or more nodes connected to the source may be merged with the source to form a larger source. Similarly, if running a max-flow min-cut algorithm over the flow graph, as discussed below, indicates that edges terminating into a sink should be removed, one or more nodes connected to the sink may be merged with the sink to form a larger sink. In certain embodiments, the edges connecting combined nodes may be disregarded. In certain embodiments, sources may be combined with nodes to form larger sources until the common faces associated with the edges emanating from the larger source have a total cross-sectional area that is larger than a threshold. In certain embodiments, this threshold may be the minimum area of tissue a clinician determines may be ablated or that is practical to ablate.

Figure 7:
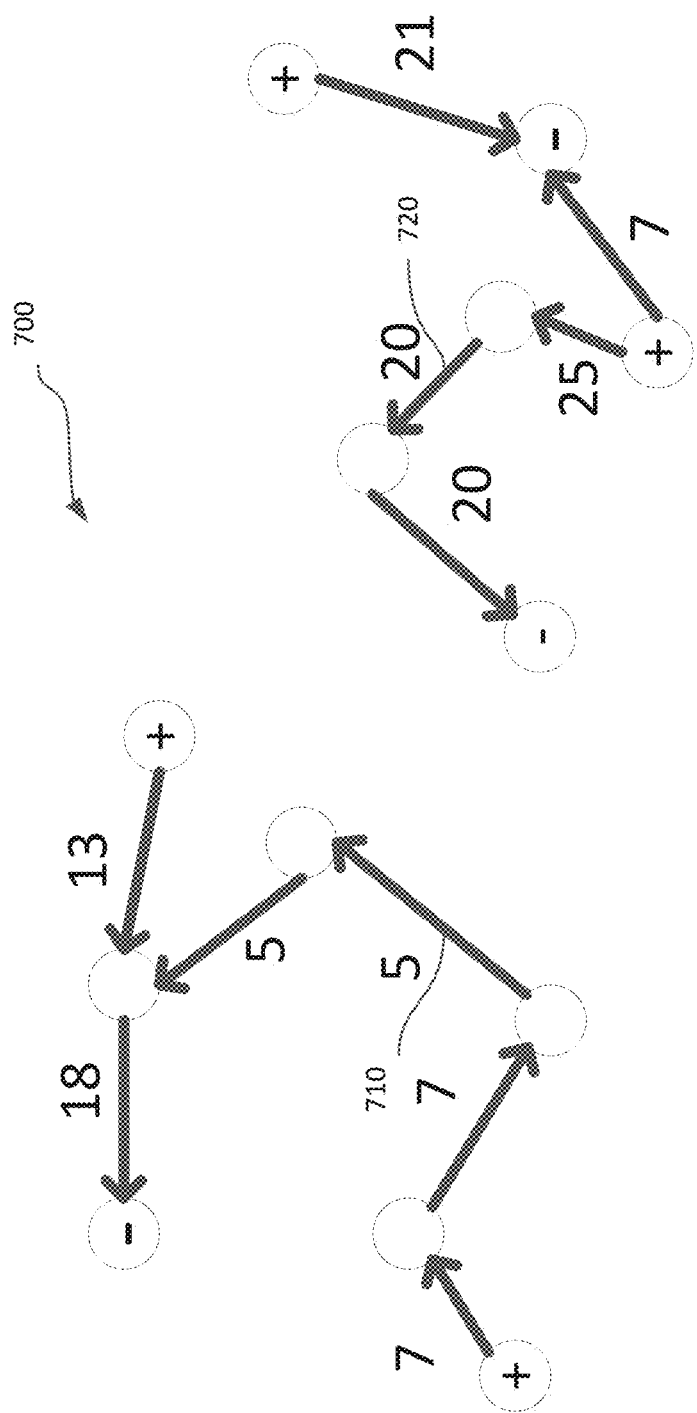
FIG. 7: Illustrates an exemplary flow graph.

The system, according to an embodiment of the disclosure, may analyze the flow graph to remove dead-end paths in the graph at step 660 and generate a flow graph without dead-end paths, such as exemplary flow graph 700 illustrated in FIG. 7. A dead-end path, such as exemplary dead-end paths identified by dotted squares 590*a*, 590*b*, and 590c of exemplary flow graph 500, may be a segment of the flow graph that, when one follows the edge directions, if the edges have directions, from a node representing an earlier-activated element to a node representing a later-activated element, the last node reached has no edges leaving the node and is not a sink. In certain embodiments, connectivity analysis may be performed to determine which pathways lead to dead ends. Such a dead-end path may indicate, for example, that a simulated electrical signal flowed from one part of the tissue to another but was blocked by one or more of a scar, other structure, or refractory tissue before the end of the simulation. Ablating a section of the tissue represented by such a dead-end path may not terminate a reentrant pathway because a reentrant pathway is not a dead-end pathway, but rather a continuous loop or circuit.

The illustrative system may determine which edges to remove from flow-graph segments connecting the source to the sink (i.e., segments that do not necessarily lead to a dead end) in order to optimally reduce flow through the flow graph to zero at step 670. A flow-graph segment connecting a source to a sink may be a collection of edges between a source and the first-encountered sink in the direction of the edges, if the edges have directions. Determining which edges to remove may be accomplished using a known MFMC algorithm, such as the Boykov-Kolmogorov algorithm. This algorithm may calculate the maximum flow through the graph, which, per the Max-flow Min-cut theorem, will also be the total edge capacity of the smallest cut (i.e., the removal of edges with the smallest sum total of their capacities) that can be made in the graph to reduce flow to zero (i.e., the min-cut). A flow is reduced to zero when, after edges are removed, no net movement may occur from the source to the sink in the flow graph. Calculating the maximum flow may comprise assigning a flow value to each edge such that net movement between the source and the sink, were movement to occur, is maximized. In certain embodiments, residual capacities may be calculated for each edge. The residual capacity calculated for an edge may be the difference between the edge's capacity and the edge's calculated maximum flow. In certain embodiments, the edges to be removed (i.e., cut) may be those with a residual capacity equal to zero. These removed edges may correspond to the common faces of elements on which optimal ablations may be indicated, informing the user where in the heart to ablate to prevent the observed reentrant activation. This process may indicate the smallest cross-sectional area necessary to ablate to prevent the observed reentrant activation. In exemplary flow graph 700, for example, edges 710 and 720 may be identified if their residual capacities are zero under maximum flow conditions and they make up segments between a source and a sink. This may be repeated for each flow-graph segment connecting a source to a sink, thereby indicating edges with residual capacities of zero for each such segment.

In certain embodiments, the common faces associated with the identified edges may be highlighted to the user on the mesh as candidates for optimal ablation at step 680. In some embodiments, edges with a capacity above a threshold capacity are not highlighted for the user. This threshold capacity may be set empirically and/or depending upon user preference, such as if the user determines an area above which areas may not be effectively covered with ablation-created lesions (e.g., more than twenty square millimeters). In some embodiments, all common faces associated with edges making up the pathways from the source to the sink may be highlighted instead or in addition to the common faces associated with the identified edges. If all common faces associated with edges making up the pathways from the source to the sink are highlighted in addition to the common faces associated with the identified edges, in certain embodiments, the common faces associated with the identified edges may be highlighted in a different manner (e.g., in a different color). In certain embodiments, arrows showing the connection between highlighted common faces may be displayed to the user to show the edge connections between the nodes corresponding to the highlighted faces, thereby indicating the electric-signal. In some embodiments, segments connecting the source and the sink that comprise a number of edges that is below a threshold number of edges are disregarded. For example, if it is considered that no reentrant activation may have a cycle length of less than 100 ms in a human heart, then flow-graph segments whose sources and sinks are connected by activation times of a duration less than 100 ms may be disregarded.

Figure 8:
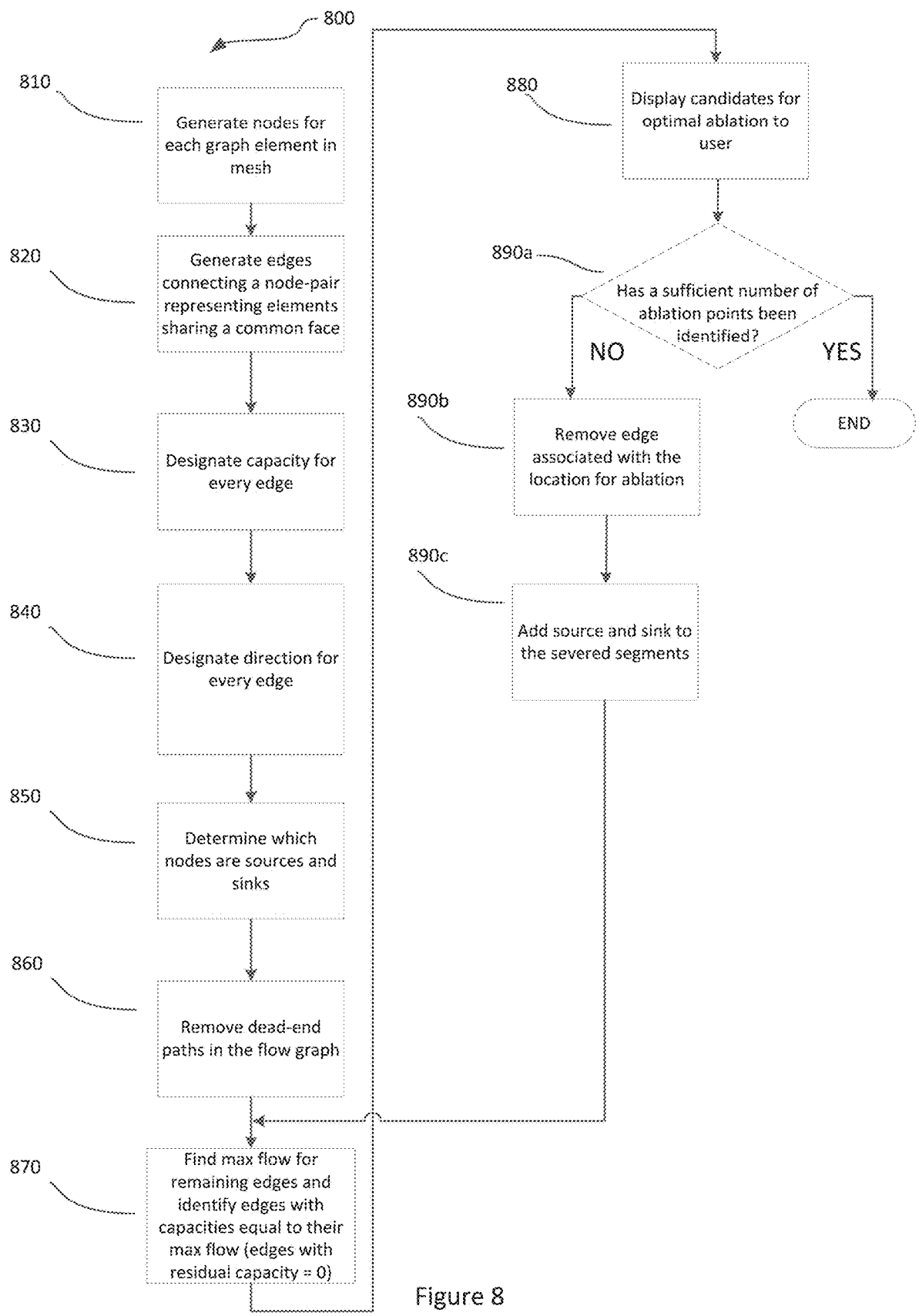
FIG. 8: Illustrates an exemplary process for identifying optimized ablation targets for treating and preventing arrhythmias sustained by reentrant circuits.
Figure 9:
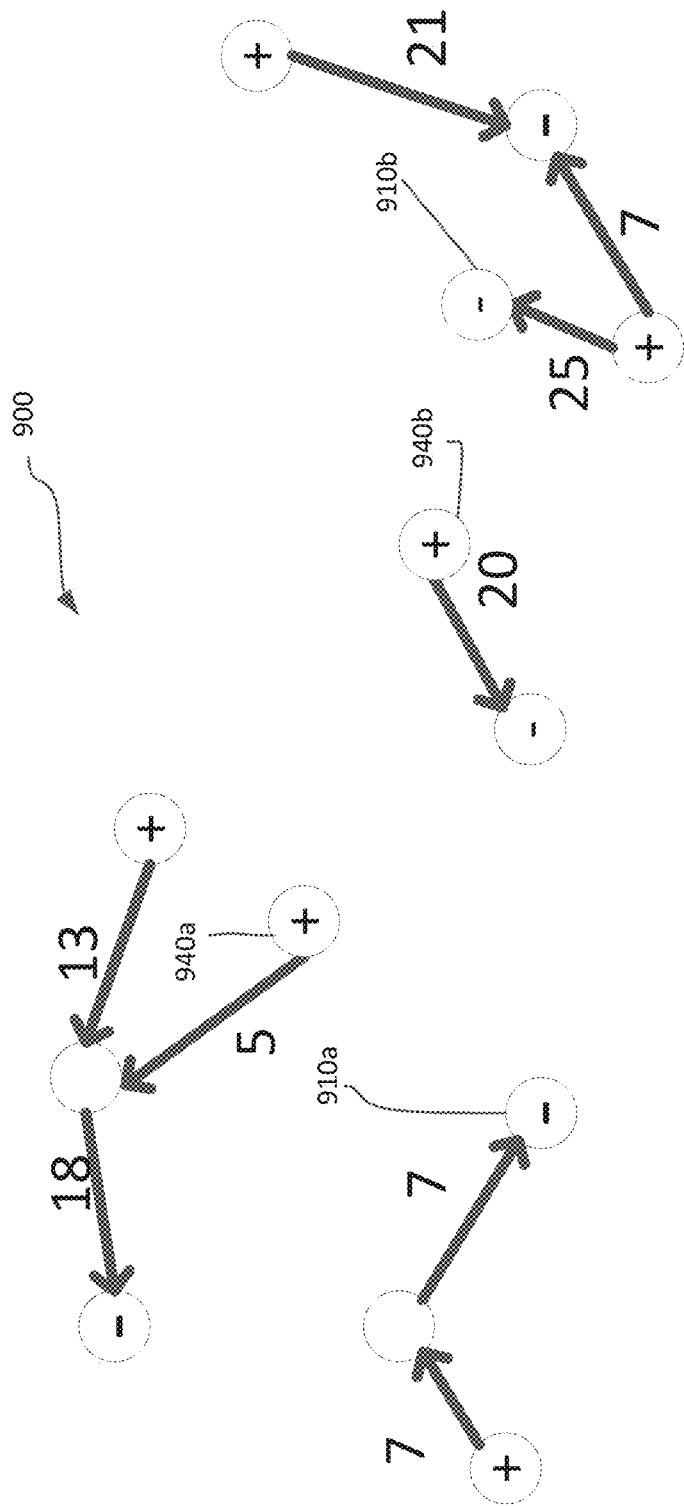
FIG. 9: Illustrates an exemplary flow graph.

In certain embodiments, after a set of edges associated with a location for ablation is identified in each segment, the segments may be severed by removing those edges and new, shorter segments may be created at steps 890a, 890b, and 890c of exemplary process 800 illustrated in FIG. 8. This may result in a flow graph similar to flow graph 900 illustrated in FIG. 9. Steps 810 through 880 of process 800 may be similar to steps 610 through 680 of process 600. Exemplary process 800 may comprise determining whether additional ablation points are to be identified at step 890a. At step 890b, if additional ablation points are to be identified, edges identified in step 870 are removed. These identified edges may be edges 710 and 720 in exemplary flow graph 700. Next, the nodes from which the removed edges emanated, such as nodes 910a and 910b, may be defined as sinks. The nodes to which the removed edges pointed, such as nodes 940a and 940b, may be defined as sources. Thus, the original sources may be connected to a new sink at the cut boundary by a flow graph and the original sink may be connected to a new source on the other side of the cut boundary. The foregoing method for finding the maximum flow through the edges and finding the edges with a residual capacity of zero and highlighting the associated common faces may be repeated for the newly created segments connecting sources and sinks. The process of creating smaller segments and finding and highlighting more locations for ablation may be repeated a set number of times or until the max flow in each newly-created segment is larger than the capacity threshold above which edges are removed. This may be done to decrease the chances of a terminated reentrant pathway being activated by a conduction pathway that was not identified by the simulation.

In certain embodiments, the foregoing methods for identifying optimized ablation targets may be performed after determining whether a reentrant pathway is detected. In an exemplary embodiment, the method may be performed based on whether a reentrant pathway is detected. A reentrant pathway may be detected by, for example, observing a point on heart tissue model under simulated stimulation for multiple activations after a fixed or variable period of time. Such period of time may be based on, for example, clinical data indicating how much time must pass after electrode stimulation for no further activations to occur. In certain embodiments, the presence of activation after this period of time may indicate the presence of a reentrant pathway.

Figure 10:
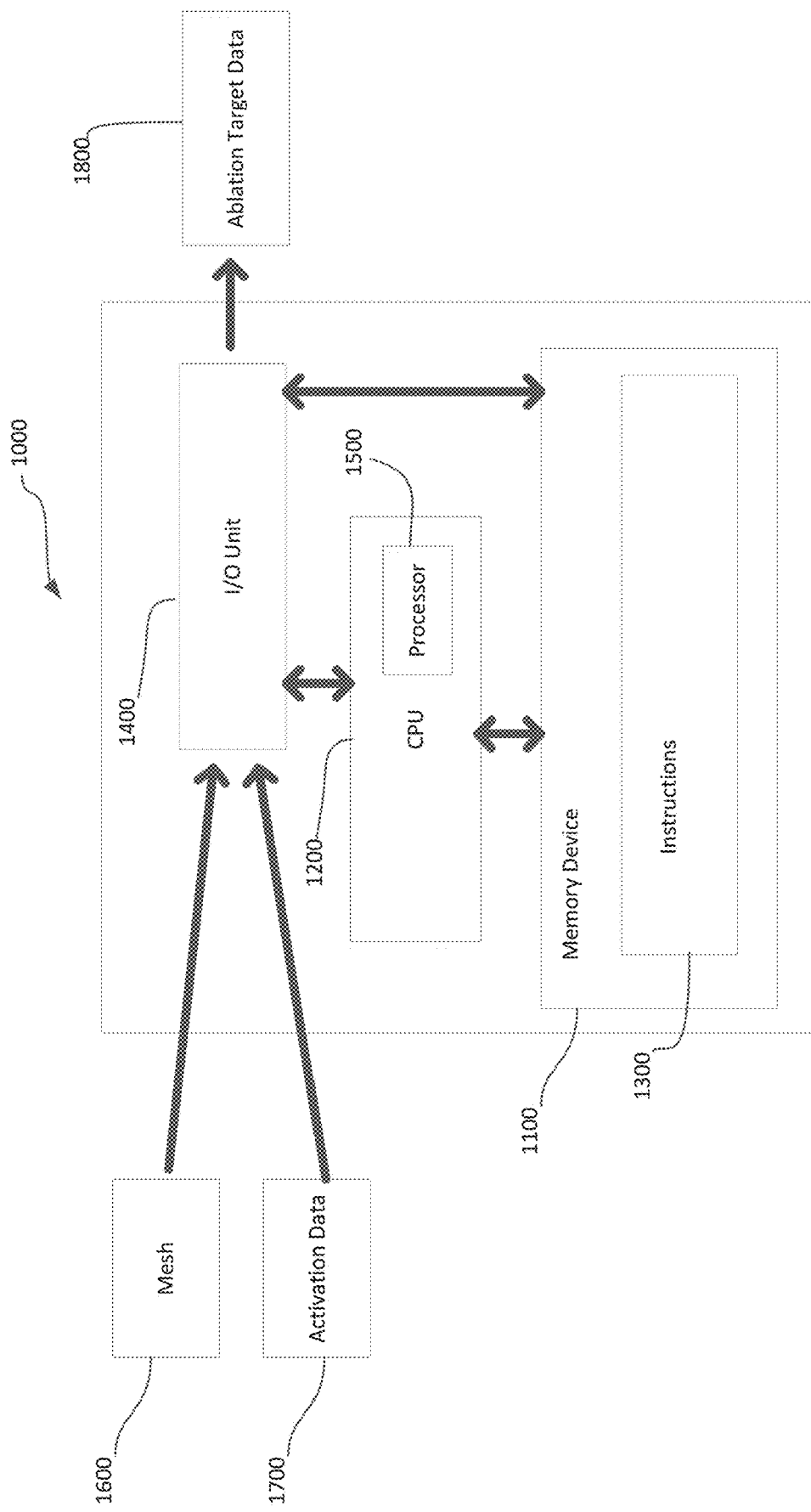
FIG. 10: Illustrates an exemplary system for identifying optimized ablation targets for treating and preventing arrhythmias sustained by reentrant circuits.

A system for identifying optimized ablation targets for treating and preventing arrhythmias sustained by reentrant circuits is illustrated in FIG. 10 as exemplary system 1000. The various components of system 1000 may include an assembly of hardware, software, and/or firmware, including a memory device 1100, a central processing unit ("CPU") 1200, and/or an optional user interface unit ("I/O Unit") 1400. Memory device 1100 may include any type of RAM or ROM embodied in a physical storage medium, such as magnetic storage including floppy disk, hard disk, or magnetic tape; semiconductor storage such as solid state disk (SSD) or flash memory; optical disc storage; or magneto-optical disc storage. The CPU 1200 may include one or more processors, such as processor 1500, for processing data according to a set of programmable instructions 1300 or software stored in the memory device 1100. The functions of each processor 1500 may be provided by a single dedicated processor 1500 or by a plurality of such processors. Moreover, the one or more processors 1500 may include, without limitation, digital signal processor (DSP) hardware, or any other hardware capable of executing software. An optional user interface ("I/O Unit") 1400 may comprise any type or combination of input/output devices, such as a display monitor, keyboard, touch screen, and/or mouse. The I/O Unit 1400 may receive mesh 1600 and activation data 1700. The processor 1500 may execute instructions 1300 causing the system to output ablation target data 1800 through the I/O Unit 1400.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. For example, some embodiments discussed above pertain to ventricular tachycardia. The systems and methods described herein may also be used to treat other types of arrhythmia, such as, for example, atrial flutter. As another example, the systems and methods for converting electrical-signal propagation data into a flow graph may be applied in other fields, such as converting the propagation of any time-varying field or energy along a physical structure into a flow graph. A MFMC algorithm may be run on such flow graph to determine an optimal way to alter the propagation along the physical structure.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Computer programs, program modules, and code based on the written description of this specification, such as those used by the microcontrollers, are readily within the purview of a software developer. The computer programs, program modules, or code can be created using a variety of programming techniques. For example, they can be designed in or by means of Java, C, C++, assembly language, or any such programming languages. One or more of such programs, modules, or code can be integrated into a device system or existing communications software. The programs, modules, or code can also be implemented or replicated as firmware or circuit logic.

Another aspect of the disclosure is directed to a non-transitory computer-readable medium storing instructions which, when executed, cause one or more processors to perform the methods of the disclosure. The computer-readable medium may include volatile or non-volatile, magnetic, semiconductor, tape, optical, removable, non-removable, or other types of computer-readable medium or computer-readable storage devices. For example, the computer-readable medium may be the storage unit or the memory module having the computer instructions stored thereon, as disclosed. In some embodiments, the computer-readable medium may be a disc or a flash drive having the computer instructions stored thereon.

Moreover, while illustrative embodiments have been described herein, the scope of any and all embodiments include equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. A method for identifying optimized regions of interest, the method comprising:
   receiving at least one patient-specific three-dimensional (3D) model of a patient's heart;
   generating activation data from one or more simulations of electrical-signal propagation over the 3D model;
   generating at least one flow graph based on the activation data and the 3D model, the flow graph comprising two or more nodes and one or more edges connecting the two or more nodes;
   determining one or more directions associated with the one or more edges; and
   determining one or more regions of interest, which correspond to a minimum number of cuts in the flow graph and a maximum flow through the flow graph, by determining one or more target edges based on their respective residual capacities, wherein the one or more target edges are identified as the one or more regions of interest.

2. The method of claim 1, wherein the one or more edges correspond to one or more capacities of movement between the two or more nodes.

3. The method of claim 2, wherein the one or more capacities represent movement of electrical signals between two or more structures associated with the two or more nodes.

4. The method of claim 3, wherein determining the one or more directions is based on cross-sectional areas of one or more common faces between the two or more structures.

5. The method of claim 1, wherein determining the one or more directions is based on an order in which the two or more nodes were activated during the one or more simulations.

6. The method of claim 1, further comprising designating a first subset of the two or more nodes as source nodes, wherein the source nodes represent nodes that only have movement coming out of them.

7. The method of claim 1, further comprising designating a second subset of the two or more nodes as sink nodes, wherein the sink nodes represent nodes that only have movement coming into them.

8. The method of claim 1, wherein the 3D model comprises two or more elements, and wherein the two or more nodes correspond to elements activated during the one or more simulations.

9. The method of claim 1, wherein the 3D model comprises two or more elements, and wherein the two or more nodes correspond to elements activated at a multiple of a predetermined period during the one or more simulations.

10. The method of claim 1, wherein the 3D model comprises two or more elements, and wherein the two or more nodes correspond to elements activated at particular times based on a function of when one or more vertices of the elements activated during the one or more simulations.

11. The method of claim 1, wherein the 3D model comprises two or more elements, and wherein the two or more nodes correspond to elements activated within a window of time during the one or more simulations.

12. The method of claim 1, wherein determining the regions of interest comprises:
determining one or more target edges with a smallest sum total of their respective capacities,
wherein removing the target edges reduces a flow through the flow graph to zero.

13. The method of claim 1, wherein the residual capacities of the one or more target edges are equal to zero.

14. The method of claim 1, further comprising:
designating a first subset of the two or more nodes as source nodes;
designating a second subset of the two or more nodes as sink nodes; and
eliminating one or more edges that do not form a part of a path from a source node to a sink node.

15. The method of claim 1, wherein the activation data comprises one or more activation times relative to start and end times of the simulations.

16. The method of claim 1, further comprising displaying the regions of interest on one or more images of the patient's heart.

17. The method of claim 1, wherein the regions of interest include one or more ablation targets.

18. A system for identifying optimized regions of interest, the system comprising:
at least one non-transitory computer-readable medium configured to store instructions; and
at least one processor configured to execute the instructions to perform operations comprising:
receiving at least one patient-specific three-dimensional (3D) model of a patient's heart;
generating activation data from one or more simulations of electrical-signal propagation over the 3D model;
generating at least one flow graph based on the activation data and the 3D model, the flow graph comprising two or more nodes and one or more edges connecting the two or more nodes;
determining one or more directions associated with the one or more edges; and
determining one or more regions of interest, which correspond to a minimum number of cuts in the flow graph and a maximum flow through the flow graph, by determining one or more target edges based on their respective residual capacities, wherein the one or more target edges are identified as the one or more regions of interest.

19. A non-transitory computer-readable medium storing a set of instructions that are executable by one or more processors to cause the processors to perform a method for identifying optimized regions of interest, the method comprising:
receiving at least one patient-specific three-dimensional (3D) model of a patient's heart;
generating activation data from one or more simulations of electrical-signal propagation over the 3D model;
generating at least one flow graph based on the activation data and the 3D model, the flow graph comprising two or more nodes and one or more edges connecting the two or more nodes;
determining one or more directions associated with the one or more edges; and
determining one or more regions of interest, which correspond to a minimum number of cuts in the flow graph and a maximum flow through the flow graph, by determining one or more target edges based on their respective residual capacities, wherein the one or more target edges are identified as the one or more regions of interest.

* * * * *